United States Patent [19]
DeLuca et al.

[11] Patent Number: 5,151,416
[45] Date of Patent: Sep. 29, 1992

[54] METHOD OF EXTERMINATING RODENTS AND OTHER VERTEBRATE PESTS

[75] Inventors: Hector F. DeLuca, Deerfield; Connie M. Smith, Madison, both of Wis.

[73] Assignee: Wisconsin Alumni Research Foundation, Madison, Wis.

[21] Appl. No.: 691,178

[22] Filed: Apr. 24, 1991

Related U.S. Application Data

[63] Continuation of Ser. No. 352,963, May 17, 1989, abandoned.

[51] Int. Cl.$^5$ .................. A01N 45/00; G07J 172/00
[52] U.S. Cl. ................................ 514/167; 552/653
[58] Field of Search .............. 514/167, 165; 552/653

[56] References Cited

U.S. PATENT DOCUMENTS

| 4,035,493 | 7/1977 | DeLuca et al. | 424/236 |
| 4,313,942 | 2/1982 | DeLuca et al. | 424/236 |

OTHER PUBLICATIONS

Chemical Abstracts, vol. 108 (1988); 126707c; Watanabe et al.
Steenbock et al., Vitamin D and Growth, Journal of Nutrition, vol. 57, Sep.–Dec. 1955, pp. 449–468.

*Primary Examiner*—Frederick E. Waddell
*Assistant Examiner*—T. J. Criares
*Attorney, Agent, or Firm*—Andrus, Sceales, Starke & Sawall

[57] ABSTRACT

A method for controlling vertebrate pest populations such as rodents, starlings and blackbirds which comprise making available to such pest populations a vitamin D compound in a high calcium bait diet.

11 Claims, 1 Drawing Sheet

METHOD OF EXTERMINATING RODENTS AND OTHER VERTEBRATE PESTS

This is a continuation of application Ser. No. 07/352,963, filed May 17, 1989, now abandoned.

BACKGROUND AND SUMMARY OF THE INVENTION

This invention relates to methods for eliminating or controlling pest populations, and more particularly to such a method which utilizes a vitamin D compound in a high calcium bait diet.

It is well known that annually rodents are responsible for the loss of as much as 10% of the grain crop in the United States and as much as 30% of the grain crop in underdeveloped countries. Rodents are also known to transfer disease, are destructive and contaminate the food supply. Many methods have been devised for eliminating and/or controlling rodents and other vertebrate pests such as starlings and blackbirds.

The most important rodenticide in recent years has been the anticoagulant series especially warfarin, sodium warfarin, and crystalline sodium warfarin. Warfarin has had the advantage of being difficult to detect in the bait, is not immediately lethal, and thus allows the animal to consume warfarin-containing bait successively and not associate the consumption of that bait with death. It has, however, significant secondary toxicity, i.e. animals poisoned with warfarin can transmit that poison upon consumption by larger animals, as for example a cat consuming rodents poisoned with warfarin. In addition, strains of rats have developed warfarin resistance.

A recent rodenticide has been the use of vitamin D which at high doses is toxic to vertebrate animals. Doses of 750 parts/million or higher are required before vitamin $D_2$ or vitamin $D_3$ will cause intoxication. Although this concentration may lead to some detection, it is low enough to be effective. The vitamin D compounds are also of considerable interest in this respect, in that they do not survive for long periods of time in the environment and hence do not present an environmental problem.

A recent important advance has been the development of 1-hydroxylated vitamins since they have much higher toxicity than ordinary vitamin D. Doses of about 15 parts/million is effective against mice, rats, and other rodents, thus eliminating possible detection since it is a tasteless compound and active in small amounts. It has the advantage of being rapidly metabolized and thus provides no secondary toxicity. Furthermore because it is present in small amounts, it is even less of an environmental problem than vitamin D itself. The most important consideration is the higher potency may well reduce the cost of the vitamin D rodenticide. A method of activating vitamin D by 1-hydroxylation has also been introduced, primarily to reduce the cost of manufacturing of 1-hydroxyvitamin $D_3$.

Rats often consume high calcium diets quite intensely. In fact, cheese must be regarded as one of the favored foods available to rats and mice. We have learned that the toxicity of vitamin D compounds is greatly increased when calcium intakes are elevated. Vitamin D compounds can therefore be made into superior rodenticides by merely providing them in a high calcium matrix or a high calcium bait diet. This invention, therefore, teaches that a superior method of eliminating pests is to provide a vitamin D compound in a high calcium bait diet. The vitamin D compound can be vitamin $D_3$, vitamin $D_2$, 1 alpha-hydroxyvitamin $D_3$, 1 alpha-hydroxyvitamin $D_2$, 25-hydroxyvitamin $D_3$, 1 alpha, 25-dihydroxyvitamin $D_3$, 1 alpha, 25-dihydroxyvitamin $D_2$, and others as well as the many new analogs which are 1 alpha-hydroxylated, as defined further herein.

DETAILED DISCLOSURE OF THE INVENTION

Figure 1:
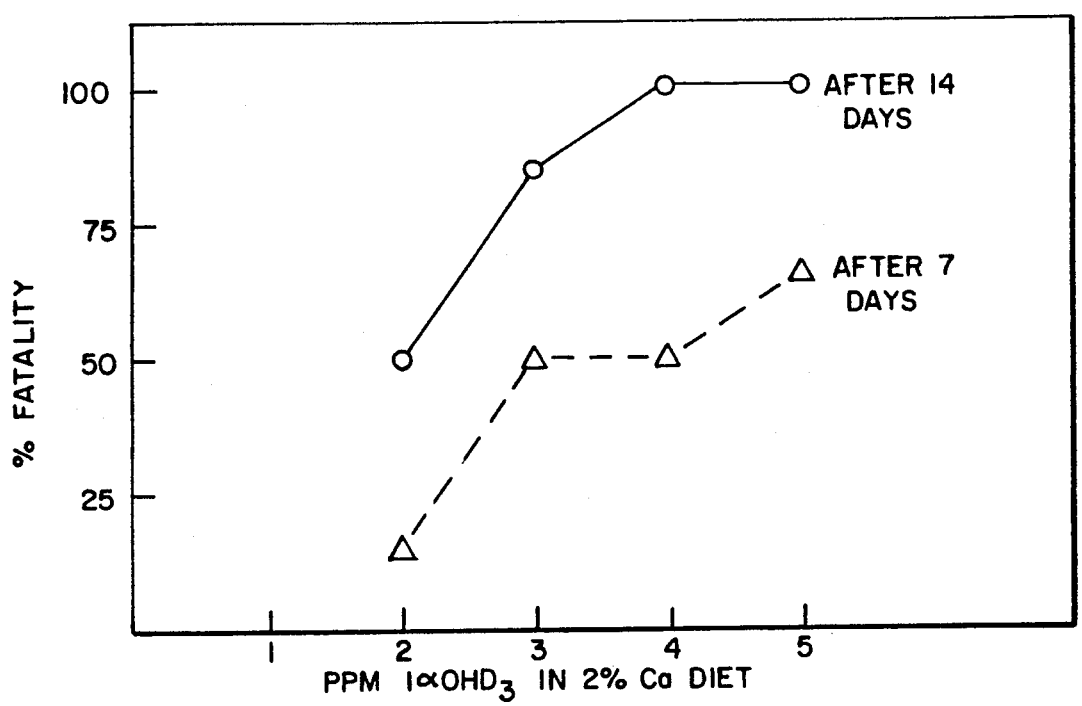
FIG. 1 is a graph illustrating the percent fatality of rats versus varying amounts of 1 alpha-hydroxyvitamin $D_3$ in a 2% calcium diet after 7 days and after 14 days.

The present invention comprises a method for controlling vertebrate pest populations such as rodents, starlings and blackbirds. The method comprises making available to such pest populations a vitamin D compound in a high calcium bait diet.

As used herein the term "vitamin D compound" encompasses compounds which control one or more of the various vitamin D-responsive processes in mammals, i.e. intestinal calcium absorption, bone mobilization, and bone mineralization. Thus the vitamin D compounds encompassed by this invention include cholecalciferol and ergocalciferol and their known metabolites, as well as the known synthetic cholecalciferol and ergocalciferol analogs which express calcemic activity. These synthetic cholecalciferol and ergocalciferol analogs comprise such categories of compounds as the 5,6-trans-cholecalciferols and 5,6-trans-ergocalciferols, the fluorinated cholecalciferols, the side chain homologated cholecalciferols and side chain homologated $\Delta^{22}$-cholecalciferols. Specific examples of such compounds include vitamin D metabolites or analogs such as vitamin $D_3$, vitamin $D_2$, 1 alpha-hydroxyvitamin $D_3$, 1 alpha-hydroxyvitamin $D_2$, 1 alpha, 25-dihydroxyvitamin $D_3$, 1 alpha, 25-dihydroxyvitamin $D_2$, 25-hydroxyvitamin $D_3$, 25-hydroxyvitamin $D_2$, 24,24-difluoro-25-hydroxyvitamin $D_3$, 24,24-difluoro-1 alpha, 25-hydroxyvitamin dihydroxyvitamin $D_3$, 24-fluoro-25-hydroxyvitamin $D_3$, 24-fluoro-1alpha, 25-dihydroxyvitamin $D_3$, 2 betafluoro-25-hydroxyvitamin $D_3$, 2 beta-fluoro-1 alphahydroxyvitamin $D_3$, 2 beta-fluoro-1 alpha,25-dihydroxyvitamin $D_3$, 26,26,26,27,27,27-hexafluoro-25-hydroxyvitamin $D_3$, 26,26,26,27,27,27-hexafluoro-1-alpha, 25-dihydroxyvitamin $D_3$, 24,25-dihydroxyvitamin $D_3$, 1 alpha, 24,25-trihydroxyvitamin $D_3$, 25,26-dihydroxyvitamin $D_3$, 1 alpha, 25,26-trihydroxyvitamin $D_3$, 1 alpha, 25-dihydroxy-24-epi-vitamin $D_2$, 24-homo-1,25-dihydroxyvitamin $D_3$ 24-dihomo-1,25-dihydroxyvitamin $D_3$ 24-trihomo-1,25-dihydroxyvitamin $D_3$ and the corresponding 26- or 26,27-homo, dihomo or trihomo analogs of 1 alpha, 25-dihydroxyvitamin $D_3$.

The vitamin D compound may be made available to a pest population either as the sole intoxicating agent or in combination with other vitamin D compounds or in combination with other agents, such as other rodenticidally effective or intoxicating substances. Doses of from about 1 part/million parts of bait diet to about 500 parts/million parts of bait diet of a vitamin D compound per se, or in combination with other vitamin D compounds, in the pest's diet for a period of about 7 days to about 15 days, the proportions of each of the compounds in the combination being dependent upon the particular pest being treated and the rate of fatality desired, are generally effective. Although the actual amount of the vitamin D compound used is not critical, in all cases sufficient amounts of the compound should be used to effect control of the pest population. Amounts in excess of about 500 parts/million parts of bait diet of the vitamin D compound, or the combination of that compound with other vitamin D compounds, in the pest's diet are generally unnecessary to achieve the desired results and may not be economically sound practice. In practice, it is understood that the specific dosage utilized in any given case will be adjusted in accordance with the specific compounds being employed, the pest to be treated, the condition of the pest and the other relevant facts that may modify the activity of the vitamin D compound or the response of the pest, as is well known by those skilled in the art.

The calcium compound employed in the high calcium diet may be in the form of calcium containing compounds i.e. in a combined form such as in calcium salts like calcium carbonate, calcium citrate, calcium phosphate, calcium gluconate, calcium lactate, calcium acetate, calcium chloride and the like. Combinations of calcium compounds may also be employed. In general, any substance, e.g. milk, containing calcium that may be metabolized by the vertebrate pest may be employed as the calcium compound ingredient in the present invention. The amount of calcium compound employed in the diet of the pest should be sufficient to represent a high calcium diet for the pest. By "high calcium diet" as used in this specification it is meant supplementing the pest's dietary calcium with calcium at a level greater than that level which is normal for the pest. In general, a normal level of calcium would represent 0.5% of the pest's diet. Accordingly, a high calcium diet for a pest would involve the administration of sufficient calcium to increase the total calcium intake in the pest's diet to represent from about 1% to about 3% or more of the diet of the vertebrate pest. However, the proportion of the calcium is dependent upon the particular pest being treated and the rate of fatality desired, with the above percentages generally effective to practice the present invention. Although the actual amount of the calcium compound used is not critical, in all cases sufficient of the compound should be used to effect control of the pest population. Amounts in the diet of the pest in excess of about 3% calcium are generally unnecessary to achieve the desired results and may not be economically sound practice. In practice, it is understood that the specific dosage utilized in any given case will be adjusted in accordance with the specific compounds being employed, the pest to be treated, the condition of the pest and the other relevant facts that may modify the activity of the calcium compound or the response of the pest, as is well known by those skilled in the art.

Dosage forms of the vitamin D and calcium compounds can be prepared by combining them with edible material acceptable to the vertebrate pest in a food bait, as is well known in the art. Such edible material may be grains, cheeses, butters, salts, milk products or may be defined material such as casein salts, sugars, vegetable or animal fats and proteins, and may either be solid or liquid. If a solid form is used the dosage form of the compounds and edible material is typically in the form of pellets, powders, biscuits, etc. If a liquid form is used, syrup or liquid suspensions, emulsions or solutions may be the dosage form. The dosage forms may also contain adjuvants, such as preserving, stabilizing, wetting or emulsifying agents, solution promoters, binders, fillers, etc.

The present invention is further described by means of the following illustrative examples.

TABLE 1

Calcium Intake Increases Rodenticide Activity of 1 alpha-Hydroxyvitamin $D_3$

| Group | Days of Consumption | | | | | Body Weight |
|---|---|---|---|---|---|---|
| | 11 | 12 | 13 | 14 | 15 | |
| Control Group 3% Ca (no D) | 0 | 0 | 0 | 0 | 0 | 318 ± 24 |
| .47% Calcium (Normal level) (5 ppm) | 0 | 1/6 | — | 4/6 | 4/6 | 185 ± 16 |
| 1.0% Calcium (5 ppm) | 1/6 | — | 3/6 | 4/6 | 4/6 | 183 ± 14 |
| 2.0% Calcium (5 ppm) | 1/6 | — | 4/6 | 4/6 | 5/6 | 196 ± 12 |
| 3.0% Calcium (5 ppm) | 4/6 | 5/6 | — | — | 6/6* | 194 ± 20 |

Experimental rats were fed a diet composed of vitamin test casein, salts, corn sugar, vegetable oil, and minerals to which was added increasing amounts of calcium according to the diet described by Suda et al (*J. Nutr.* 100, 1049–1052, 1970). Calcium was added to the diet in the form of calcium carbonate. Calcium carbonate was added at the expense of the corn sugar to achieve the indicated percent calcium in the diet as shown in Table 1.

Six rats in each group were placed on a 3% calcium diet to which was added no vitamin D. All other groups had incorporated in their diet 5 parts/million 1 alpha-hydroxyvitamin $D_3$. They were fed for 15 days on these diets. As shown in Table 1, the control group receiving only the 3% calcium diet showed no toxicity, and the animals maintained their normal body weight during the 15-day feeding period. On the other hand, with increasing calcium content of the diet, the toxicity of the 5 parts/million 1 alphahydroxyvitamin $D_3$ increased progressively and at 3% calcium, 4 of the 6 animals had already died by day 11 of feeding the 5 parts/million 1 alpha-hydroxyvitamin $D_3$ and the 3% calcium diet. The results illustrate that the toxicity of 5 parts/million 1 alphahydroxyvitamin $D_3$ is significantly increased by increasing calcium of the bait diet.

Figure 2:
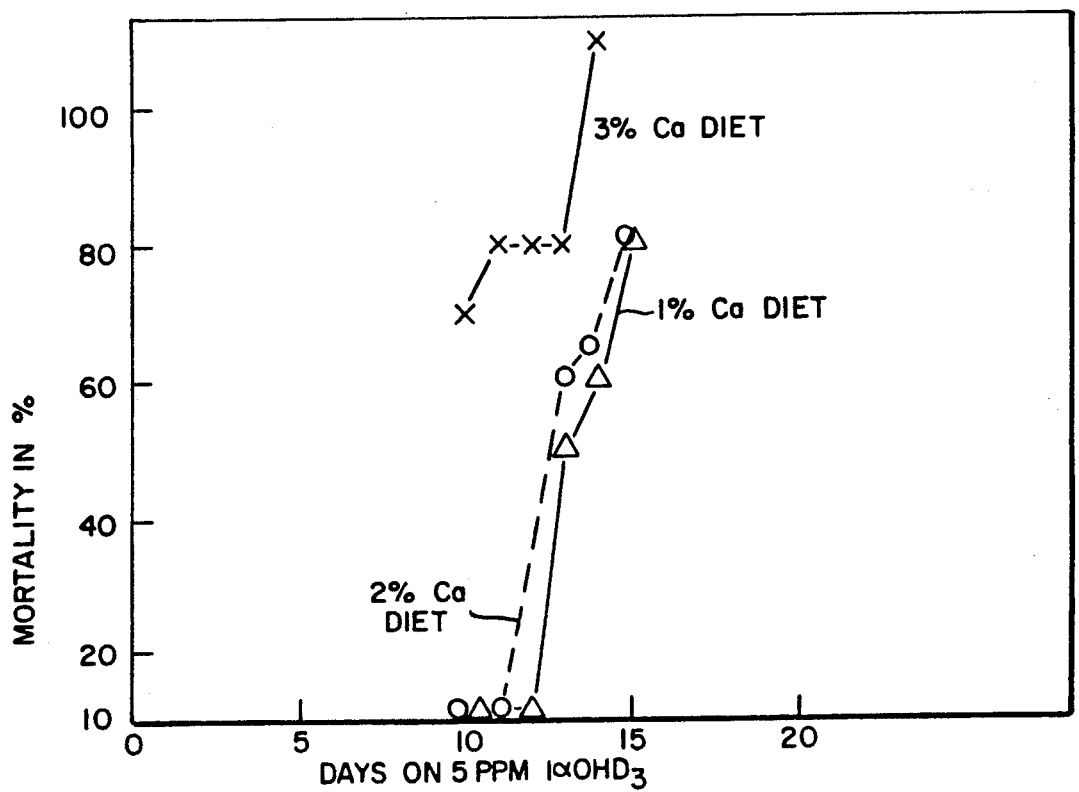
FIG. 2 is a graph illustrating the percent fatality of rats versus time as a result of incorporating 5 parts/million of 1 alpha-hydroxyvitamin $D_3$ in a 1%, 2%, and 3% calcium diet.

As shown in FIG. 1, 4 parts/million 1 alpha-hydroxyvitamin $D_3$ added to a 2% calcium diet results in 100% fatalities to the animals after 14 days of feeding and 50% after 7 days of feeding. This is to be contrasted with the fact that 15 parts/million of 1 alpha-hydroxyvitamin $D_3$ is required to kill the animals under normal bait conditions. As shown in FIG. 2, the toxicity of 5 parts/million 1 alpha-hydroxyvitamin $D_3$ is much higher in the 3% calcium diet than in either the 1% or 2% calcium diet.

Various modes of carrying out the invention are contemplated as being within the scope of the following claims particularly pointing out and distinctly claiming the subject matter regarded as the invention.

We claim:

1. A method for controlling vertebrate pest populations which comprises making available in a diet of such populations edible material acceptable to the vertebrate pest, which edible material contains ingredients toxic to said pest, said toxic ingredients consisting of 1α-hydroxyvitamin $D_3$ in an amount of from about 4 parts per million to about 5 parts per million and calcium in an amount of from about 2% to about 2.6% by weight in said diet.

2. The method of claim 1 wherein said calcium is in the form of calcium carbonate.

3. The method of claim 1 wherein said vitamin D compound and said calcium are simultaneously made available to said pest populations.

4. The method of claim 1 wherein said diet is made available to rodents.

5. The method of claim 1 wherein said diet is made available to starlings.

6. The method of claim 1 wherein said diet is made available to blackbirds.

7. A method for controlling vertebrate pest populations which comprises making available in the diet of such populations, in amounts sufficient to effect control, a food bait consisting essentially of edible material acceptable to such pest populations, 1α-hydroxyvitamin $D_3$ is an amount from about 4 parts per million to about 5 parts per million and a calcium compound that provides calcium at about 2% to about 2.6% by weight as ingredients thereof.

8. The method of claim 7 wherein said calcium is in the form of calcium carbonate.

9. The method of claim 1 wherein said bait is formulated for rodents.

10. The method of claim 1 wherein said bait is formulated for starlings.

11. The method of claim 1 wherein said bait is formulated for blackbirds.

* * * * *

UNITED STATES PATENT AND TRADEMARK OFFICE
CERTIFICATE OF CORRECTION

PATENT NO. : 5,151,416

DATED : September 29, 1992

INVENTOR(S) : HECTOR F. DeLUCA ET AL

It is certified that error appears in the above-identified patent and that said Letters Patent is hereby corrected as shown below:

| | |
|---|---|
| Claim 1<br>Column 5, Line 1 | After "consisting" insert --- essentially --- |
| Claim 7<br>Column 6, Line 6 | Delete "is" and substitute therefore --- in --- |
| Claim 9<br>Column 6, Line 12 | Delete "1" and substitute therefore --- 7 --- |
| Claim 10<br>Column 6, Line 14 | Delete "1" and substitute therefore --- 7 --- |
| Claim 11<br>Column 6, Line 16 | Delete "1" and substitute therefore --- 7 --- |

Signed and Sealed this

Twenty-eighth Day of September, 1993

Attest:

BRUCE LEHMAN

*Attesting Officer*        *Commissioner of Patents and Trademarks*

UNITED STATES PATENT AND TRADEMARK OFFICE
CERTIFICATE OF CORRECTION

PATENT NO. : 5,151,416
DATED : September 29, 1992
INVENTOR(S) : HECTOR F. DELUCA et al It is certified that error appears in the above-identified patent and that said Letters Patent is hereby corrected as shown below:

Column 1, after line 6 and before line 8, insert the following:
--- This invention was made with United States Government support awarded by the National Institutes of Health (NIH), Grant No. DK-14481. The United States Government has certain rights to this invention.---

Signed and Sealed this

Thirty-first Day of May, 1994

Attest:

BRUCE LEHMAN

Attesting Officer          Commissioner of Patents and Trademarks